United States Patent
Kuhn et al.

(10) Patent No.: US 6,478,748 B1
(45) Date of Patent: Nov. 12, 2002

(54) MEDICAL TELEMETRY SYSTEM

(75) Inventors: Jens Kuhn, Manebach; Hans-Ullrich Marquardt, Unterpoerlitz, both of (DE)

(73) Assignee: Geratherm Medical AG, Geschwenda (DE)

( * ) Notice: Subject to any disclaimer, the term of this patent is extended or adjusted under 35 U.S.C. 154(b) by 0 days.

(21) Appl. No.: 09/674,284

(22) PCT Filed: Apr. 29, 1999

(86) PCT No.: PCT/DE99/01287

§ 371 (c)(1),
(2), (4) Date: Oct. 30, 2000

(87) PCT Pub. No.: WO99/55221

PCT Pub. Date: Nov. 4, 1999

(30) Foreign Application Priority Data

Apr. 30, 1998 (DE) .......................................... 198 19 521

(51) Int. Cl.[7] .................................................. A61B 5/00
(52) U.S. Cl. ........................................ 600/549; 600/100
(58) Field of Search ........................................ 600/549

(56) References Cited

U.S. PATENT DOCUMENTS

| | | | |
|---|---|---|---|
| 3,710,778 A | * | 1/1973 | Cornelius .................. 600/353 |
| 4,503,862 A | | 3/1985 | Baessler |
| 4,559,954 A | | 12/1985 | Murase |
| 4,608,994 A | | 9/1986 | Ozawa et al. |
| 5,687,717 A | | 11/1997 | Halpern et al. |
| 5,724,025 A | | 3/1998 | Tavori |
| 5,833,623 A | * | 11/1998 | Mann et al. ................. 600/523 |
| 5,957,854 A | * | 9/1999 | Beson et al. ................ 600/509 |

FOREIGN PATENT DOCUMENTS

| | | |
|---|---|---|
| DE | 3219558 | 12/1983 |
| DE | 4441083 | 11/1996 |
| EP | 0 808 705 | 11/1982 |
| EP | 0 195 207 | 1/1986 |
| EP | 0 796 588 | 2/1997 |
| WO | WO 86/10595 | 3/1986 |
| WO | WO 89/09021 | 10/1989 |

* cited by examiner

Primary Examiner—Kevin Shaver
Assistant Examiner—Pamela Wingood

(57) ABSTRACT

Disclosed is a medical telemetry system for collecting vital data, specifically body temperature, the system consisting of a plurality of measuring sensors 10 and a collecting device 30. Each sensor 10 is placed at a predetermined location of the patient's body and automatically detects the vital data value to be measured. Upon a measurement termination signal, which is preferably acoustical, the sensor can be removed from the measuring location and stored away. For a defined period of time, e.g. two hours, the sensor 10 remains in an active state in which it transmits the detected measured value upon request. The measured value along with an ID code and status signals, which relating for instance to the battery voltage, can be interrogated and stored by means of a collecting device 30. Upon expiry of the defined period of time, the measured value is cleared, and the sensor 10 is automatically reset to an energy-saving rest condition.

14 Claims, 1 Drawing Sheet

MEDICAL TELEMETRY SYSTEM

DESCRIPTION

Figure 1:
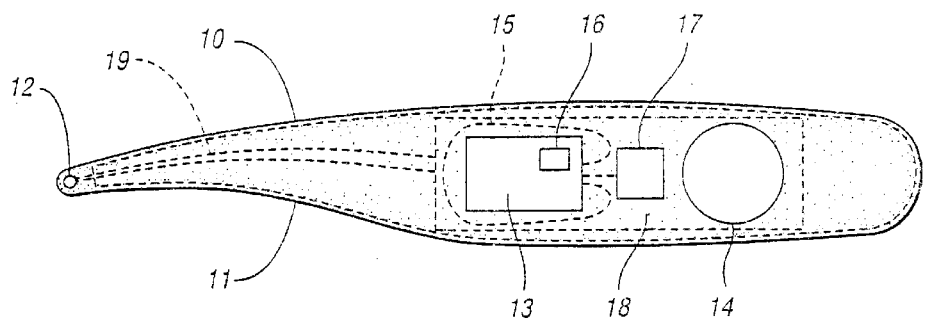

Three types of apparatus are nowadays in use for taking routine measurements of human temperature in hospitals: analogous, electronic and infrared clinical thermometers.

The conventional analogous liquid-glass clinical thermometers operate on the basis of the temperature-dependent expansion of a liquid metal, specifically mercury. Measurements may be taken in the axilla, mouth or rectum. Reading the measured temperature value and resetting the thermometer by shaking the thermometer is usually done by medical personnel. These thermometers are inexpensive, and, due to the glass body, may be disinfected without problem. Disadvantages, however, reside in the fragility of the body, in the relative poor readability of the measurement results, and in the frequency such thermometers are stolen by patients and clinical personnel.

Compact electronic clinical thermometers operate on the basis of the temperature-dependent change of resistance of a thermistor. These thermometers have a body of plastics material. These thermometers also permit measurements to be taken in the axilla, mouth or rectum. Prior to taking a measurement, the medical personnel is required, for hygienic reasons, to provide thermometers of this type with a cover. This causes additional cost and produces special refuse. The thermometers are almost unbreakable, well readable and only little more expensive than analogous clinical thermometers. However, they also are frequently stolen.

Infrared clinical thermometers measure the temperature-dependent radiation of the tympanic membrane. They operate fast but are available for measurements in the ear only, and the medical interpretation of the measurement result is not always without problem. Again, hygienic considerations require these thermometers to be provided with a fresh protective cover prior to every measurement. Placing the thermometer at the measurement location requires trained personnel and may, in case of repeated measurements, cause injure and pain. Clinical thermometers of this type are less suited for private use and, as a consequence, are not stolen. They are, however, substantially more expensive than analogous and electronic clinical thermometers.

Specific methods of electronically measuring the body temperature involve telemetric systems, such as are known from DE 3 219 558 A1, DE 4 441 083 C1, U.S. Pat. No. 4,503,862, and U.S. Pat. No. 4,865,044. These systems include a measuring probe (the thermometer proper) to be disposed on or in the patient and a separate evaluation unit.

In the system of DE 3 219 558 A1, a micro probe is implanted in the body and supplied with energy for the measurement by means of a high frequency field. The transmission of the measured value is done by absorption modulation of the HF field. Due to the small size of the measuring probe, it is difficult to supply the probe with the energy required for the measurement and for the transmission of the measured value. It is therefore necessary to expose the patient to a very strong electromagnetic field. The measuring probe is switched on and off by turning on and off the HF field. Measured values can be transmitted only when the probe is on the patient. The system is unsuited for routine measurements in a hospital.

In the system according to DE 4 441 083 C1, a telemetric measuring probe is included in an adhesive plaster which is placed on the desired location of the patient's skin. In addition to the fact that this type of placement is unsuited for measuring body temperatures at the usual locations, the patient's skin is unnecessarily irritated by the possibly repeated application and removal of plasters as would be required for taking routine measurements. Also, undesired special refuse is produced. Further, changing the plaster involves work for the nursing personnel. The provision of a largesize antenna in the form of a pillow to be placed under the patient, as recommended in this document, is expensive and hardly practical for hygienic reasons. Also, the measuring probe operates in this system only within a high frequency field and yields meaningful measurement results only if the probe is placed on the patient.

U.S. Pat. No. 4,503,862 describes a system in accordance with the first part of claim 1, wherein each patient is given his own battery-powered measuring sensor. On her round, the nurse carries a receiver unit from one patient to the next and actuates the transmitter of the respective sensor next to the receiver unit to transmit the detected temperature value. This process must be repeated for every individual. patient. As a disadvantage of this system, the sensor produces correct measurement results only if placed on the patient. The detected data must be allocated to the individual patients manually, e.g. by means of a listing.

The temperature monitoring system proposed in U.S. Pat. No. 4,865,044 uses a plurality of telemetric sensors. When a predetermined threshold value is exceeded, these sensors transmit continuously and in predetermined intervals their identification number and a modulated signal which corresponds to the measured temperature. As a disadvantage, once the starting condition has been reached, the sensors transmit continuously irrespective of whether the receiver unit is turned on and whether the sensors are within the range of the receiver unit. To save energy, it has been proposed to turn on and off the sensors periodically. When the period is relatively short, updated measurement values may be obtained virtually continuously, but this results in a high energy consumption. A long period reduces the energy consumption, but the waiting time until the moment the next actual measurement value is received may become relatively long. Since no provision is made to collect the detected temperature data selectively, the system is unsuited for routine temperature measurements in hospitals.

It is a general object of the invention to provide a medical telemetry system for vital data, specifically for taking routine measurements of the body temperature, which system avoids the disadvantages of the prior art explained above. A more specific object may be considered to reside in permitting measurement of the body temperature at the usual measurement locations at low expenses, (i.e. low cost per measurement), minimum labor for the nursing personnel, maximum safety of the data, and high comfort for the patient.

This object is met by the medical telemetry system set forth in claim 1. In the system according to the invention, the individual measuring sensors continuously and automatically monitor a predetermined threshold value and start a measurement when this threshold value is exceeded. The measured value is stored in the sensor and transmitted upon request from a collecting device.

When admitted to a hospital, every patient is given his own measuring sensor. Within an agreed period of time, the patients place their personal measuring sensor at the intended measuring location. When the measurement has been taken, the patient can remove the measuring sensor from the measuring location and store it in a holder provided for this purpose. Even after the measurement, the sensor remains active over a defined period of time during which it stores the measured value and transmits it upon receipt of a request signal. Nursing personnel is required only for collecting the measurement values stored in the measuring sensors, which is done by means of a collecting device that needs to be taken only close to the individual measuring sensors in order to collect the measured value telemetrically upon transmission of the request signal. There is thus no need to touch either the patient or the sensor, which is of advantage particularly in case of highly contagious diseases. Moreover, it is not at all necessary for the patient to be present at the time the measured value is collected. Since the measuring sensor has no display of its own, it is useless as a measuring device for private purposes, which should have a great influence on the disappearance of thermometers in hospitals.

The embodiment of claim 2 is useful because the patient does not have to place the measuring sensor into operation, and there is the additional advantage that no mechanical keys or switches with corresponding openings in the sensor body are required. This improves especially the hygienic properties of the sensor body.

The embodiment of claim 3 realises a maximum thermometer system as is common for routine temperature measurements.

The embodiment provided in accordance with claim 4 offers high comfort for the patient who needs to leave the measuring sensor at the measuring location for only a minimum period of time.

The feature of claim 5 can be useful in that measured values can be evaluated in minimum time.

The ID code of claim 6 which is transmitted along with the data ensures a unique and unambiguous association of the measurement results received by the collecting device to the individual patients.

In accordance with claim 7, since the values, which are not collected within a predetermined period of time, are cleared, confusion between "old" and "new" measured values is safely excluded. In accordance with claim 8, the erasing can be done immediately upon the transmission of the respective measured value.

The embodiment of the invention in accordance with claim 9 has the advantage that the outer appearance of the measuring sensor corresponds to that of a conventional clinical thermometer so that the patients have no difficulty to take their own measurements as usual. At the same time, the thermometer body is suited for receiving a sufficiently powerful battery and powerful antenna, which is of advantage for the signal transmission.

The development of the invention set forth in claim 10, according to which the sensor is shaped so that the sensor body can be sterilised when changing the patient, improves the hygienic aspect when taken routine measurements of the body temperature in a hospital.

Claims 11 and 12 relate to the possibility of transmitting and displaying, on the collecting device, information concerning the condition of the individual sensors in addition to the measured values proper. This information chiefly includes the charging condition of the battery. When the voltage drops below a critical value, the user is given information that the battery must be changed. In addition to this status information, it is possible to transmit, e.g., a reference count characteristic of the overall function of the measuring sensor. If this count changes towards values outside a range defined as normal, malfunction of the device may be displayed in any suitable way, e.g. on a display of the collecting device.

The further developments of the invention set forth in claims 13 to 15 result in further reduced labor for the nursing personnel.

Figure 2:
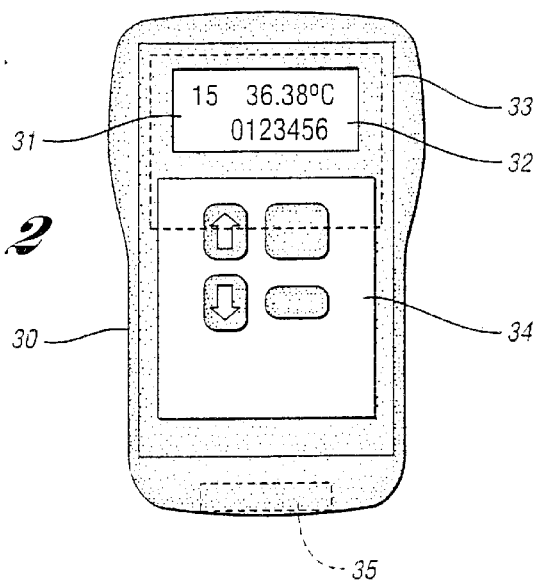
Figure 3:
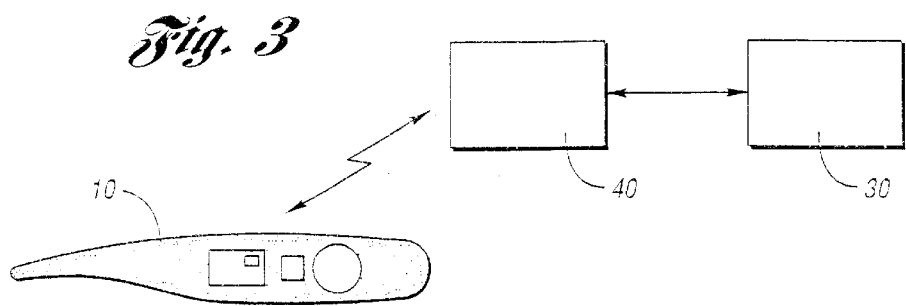

Preferred embodiments of the invention will now be explained with reference to the drawing. In the drawing, FIG. 1 shows a sensor, FIG. 2 shows a collecting unit for use in connection with sensors in accordance with FIG. 1, and FIG. 3 shows a modification of the overall telemetry system.

The sensor 10 shown schematically in FIG. 1 has a body 11 the outer shape of which corresponds to that of a traditional liquid-glass clinical thermometer or compact electronic clinical thermometer. The body 11 is entirely sealed externally and is made of a synthetic material which permits disinfection or sterilisation.

A temperature sensitive measuring element 12, e.g. a thermistor, is disposed at the end of a narrower part of the body 11, the overall shape of which is somewhat rod-like.

The larger-diameter portion of the body 11 includes an electronic measurement and control circuit 13, a battery 14, an antenna 15, a memory 16 and a, preferably acoustic, signalling device 17. The components 13 to 17 are disposed on a common circuit board 18 mounted inside the body 11. The measuring element 12 is connected to the measurement and control circuit 13 by means of connecting wires 19. Further connecting lines between the components 13 to 17 are provided on the circuit board 18 but now shown in the drawing.

In FIG. 1, the antenna 15 is shown merely schematically as an area taking up part of the circuit board 18. In a practical embodiment, the antenna 15 may extend in one or a plurality of loops around the entire outer periphery of the circuit board 18 to increase the effective surface of the antenna.

The collecting device 30 schematically shown in FIG. 2 includes a processor 31, a display 32, e.g. of the liquid crystal type, an antenna 33, a keyboard 34 and external terminals 35.

In practical use, each patient is given his own sensor 10 when admitted to the hospital. The nursing personnel records, in a listing or in any other suitable manner, the association between the patient and the ID code of the sensor. At predetermined times, e.g. between 8 and 9 a.m. or upon request by the nursing personnel, the sensor 10 is placed at the predetermined measuring location. Most patients would be in a position to do this themselves. No turn-on or control operations are necessary. The presence of nursing personnel is unnecessary also during the warming-up phase of the measuring element.

The sensors 10 continuously monitor a fixed threshold value (e.g. 32° C. in case of measuring body temperatures) and automatically start the actual measurement when this value is exceeded.

Upon termination of the measurement, which is signalled acoustically by the signalling device 17, the patient may remove the sensor 10 from the measuring location and store it in a prepared holder until the next measurement is taken. No intermediate manipulation is required, such as shaking down the mercury column of conventional medical thermometers.

At any desired time within a wide time window (e.g. two hours) after the start of the measurement, a nurse will take the collecting device 30 near the patient's sensor 10 at a distance of 1 to 2 meters. By actuation of a CALL key on the keyboard 34, a request signal is transmitted from the antenna 33 of the collecting device 30 to the measurement and the control circuit 13 of the sensor 10, which thereupon transmits the value measured by the measuring element 12 via the antenna 15.

At the same time, an ID code, which is stored in the memory 16 of the sensor 10, is transmitted. The measured value is thus automatically linked to an identification of the transmitting sensor 10 and thus to the respective patient. The measured value is displayed in connection with the ID code on the display 32 of the collecting device 30.

Prior to, or simultaneously with, the transmission of the measured value from the sensor 10 to the collecting device 30, one or a plurality of status signals are transmitted which are representative of the function of the sensor 10, particularly the charging condition of the battery 14. The display 32 of the collecting device 30 will display a message, e.g. "ERROR" in case the sensor 10 is out of order, and e.g. "LOW BAT" in case of insufficient battery voltage.

If required, the measured value, ID code and status signals may be further transmitted via the terminals 35 or via another wireless transmitting channel to a PC, a printer, a further collecting unit 30, or a remote reading device.

Collecting the measured value of an entire hospital section using the collecting device 30 occupies the nursing personnel only a few minutes. All measured values are unmistakably stored by their linking to the ID code of the sensors 10 and can be entered by the nursing personnel into patients' files at any time of the working day.

To this end, the personnel selects the various data records by operating the UP and DOWN keys on the keyboard 34 of the collecting device 30. When all data have been transferred, the entire measured-value memory of the collecting device 30 is cleared by pressing the CLEAR key. This insures that in each round only those measured values which have actually been interrogated, are stored in the collecting device 30. Sensors 10 which are missing, are out of order or have not been interrogated, are not entered in the record list of the collecting device 30.

When the patient is dismissed from the hospital, the sensor 10 is collected and disinfected or sterilised and thus prepared for subsequent use. Infections by contaminated sensors are thereby safely excluded.

Synthetic thermometer covers, which are nowadays widely used to avoid cross-contamination, are rendered superfluous with the medical telemetry system of the present invention, thus avoiding special refuse in addition to involving a considerable cost advantage. Moreover, the sensor is unattractive for both patients and nurses, so that theft should be infrequent.

In the development schematically shown in FIG. 3, an intermediate station 40 is installed in the patients' room. At given times, the patients are requested by an optical and/or acoustical signal via the intermediate station 14 to place their sensors 10. Upon termination of the measuring process, the intermediate station 40 automatically interrogates the measured values along with the ID codes and status signals and transmits them to a central collecting device 30.

What is claimed is:

1. A medical telemetry system for collecting vital data including patients' body temperatures, the system comprising a plurality of measuring sensors and collecting device, each said sensor including:
    measuring means for performing measurement cycles to detect values of vital data;
    memory means for storing the value detected in the last measurement cycle performed by said measuring means;
    means for transmitting the last detected value in response to a request signal received from said collecting device;
    clearing means for automatically removing the stored value from said memory means, and;
    means for continuously supervising a threshold value and starting a measurement cycle when said threshold value is exceeded.

2. The telemetry of claim 1, wherein the sensor includes means for terminating the measurement cycle when the gradient of change of the value detected by said measuring means falls below a predetermined value.

3. The telemetry system of claim 2, wherein said sensor includes means for producing a measurement cycle termination signal perceptible by the patient.

4. The telemetry system of claim 2, wherein said sensor includes means for transmitting a measurement cycle termination signal to said collecting device.

5. The telemetry system of claim 1, wherein said memory means further holds an ID code of said sensor and said transmitting means is adapted to transmit said ID code along with said detected value.

6. A medical telemetry system for collecting vital data including patients' body temperatures, the system comprising a plurality of measuring sensors and collecting device, each said sensor including:
    measuring means for performing measurement cycles to detect values of vital data;
    memory means for storing the value detected in the last measurement cycle performed by said measuring means;
    means for transmitting the last detected value in response to a request signal received from said collecting device;
    clearing means for automatically removing the stored value from said memory means, and;
    means for actuating said clearing means upon expiry of a predetermined period of time following a measurement cycle.

7. A medical telemetry system for collecting vital data including patients' body temperatures, the system comprising a plurality of measuring sensors and collecting device, each said sensor including:
    measuring means for performing measurement cycles to detect values of vital data;
    memory means for storing the value detected in the last measurement cycle performed by said measuring means;
    means for transmitting the last detected value in response to a request signal received from said collecting device;
    clearing means for automatically removing the stored value from said memory means, and;
    means for actuating said clearing means upon transmission of said last detected value.

8. A medical telemetry system for collecting vital data including patients' body temperatures, the system comprising a plurality of measuring sensors and collecting device, each said sensor including:
    measuring means for performing measurement cycles to detect values of vital data;
    memory means for storing the value detected in the last measurement cycle performed by said measuring means;

means for transmitting the last detected value in response to a request signal received from said collecting device; and clearing means for automatically removing the stored value from said memory means, wherein at least one sensor comprises an elongated sensor body resembling the body of a conventional clinical thermometer.

9. The telemetry system of claim 8, wherein said sensor body is sterilizable.

10. The telemetry system of claim 5, wherein said sensor includes means for producing a status signal indicative of a function of the sensor.

11. The telemetry system of claim 10, wherein said collecting device includes means for visually displaying the detected value, said ID code and said status signal of a transmitting sensor.

12. A medical telemetry system for collecting vital data including patients' body temperatures, the system comprising a plurality of measuring sensors and collecting device, each said sensor including:

measuring means for performing measurement cycles to detect values of vital data;

memory means for storing the value detected in the last measurement cycle performed by said measuring means;

means for transmitting the last detected value in response to a request signal received from said collecting device;

clearing means for automatically removing the stored value from said memory means, and;

the telemetry system further including an intermediate station disposed within a range of transmission of said plurality of sensors for relaying the signals transmitted by each sensor to said collecting device.

13. The telemetry system of claim 12, wherein said intermediate station includes means for producing a measurement request signal perceptible by the patients.

14. The telemetry system of claim 12, wherein said intermediate station includes means for transmitting a clearing signal to actuate the clearing means of a sensor upon receipt of the detected value from said sensor.

* * * * *